(12) United States Patent
Anzalone et al.

(10) Patent No.: US 8,710,256 B2
(45) Date of Patent: Apr. 29, 2014

(54) PROCESS FOR THE PREPARATION OF PROTECTED L-ALANINE DERIVATIVES

(75) Inventors: Luigi Anzalone, West Chester, PA (US); Penina Feibush, Ambler, PA (US); Frank J. Villani, Perkasie, PA (US)

(73) Assignee: Janssen Pharmaceutica, N.V., Beerse (BE)

( * ) Notice: Subject to any disclaimer, the term of this patent is extended or adjusted under 35 U.S.C. 154(b) by 170 days.

(21) Appl. No.: 12/606,730

(22) Filed: Oct. 27, 2009

(65) Prior Publication Data
US 2010/0145090 A1 Jun. 10, 2010

Related U.S. Application Data

(60) Provisional application No. 61/108,649, filed on Oct. 27, 2008.

(51) Int. Cl.
C07C 255/58 (2006.01)
C07C 253/30 (2006.01)
C07C 227/18 (2006.01)
C07C 229/34 (2006.01)

(52) U.S. Cl.
USPC .......................................... 558/359; 562/450

(58) Field of Classification Search
USPC .......................................... 558/359; 562/450
See application file for complete search history.

(56) References Cited

U.S. PATENT DOCUMENTS

| 5,554,753 A | 9/1996 | O'Donnell et al. |
| 2005/0203143 A1 | 9/2005 | Breslin et al. |
| 2006/0211861 A1 | 9/2006 | Cai et al. |

FOREIGN PATENT DOCUMENTS

WO  WO 96/06855  3/1996

OTHER PUBLICATIONS

International Search Report and the Written Opinion, dated Apr. 13, 2010, 7 pages.
Jackson, R.F., et al.: "Concise Synthesis of Enantiomerically Pure Phenylalanine, Homophenylalanine, and Bishomophenylalanine Derivatives using Organozinc Chemistry: NMR Studies of Amino Acid-Derived Organozinc Reagents" Journal of Organic Chemistry, American Chemical Society, Easton,; US LNKD-DOI: 10.1021/J0981133U, vol. 63, Jan. 1, 1998, pp. 7875-7884, XP002246452, ISSN: 0022-3263, Schemes 1,2,5; experimental section.
Schmidt, B., et al: "Preparation of N-Boc-(2,6-Bis-(ethoxycarbonyl)pyridin-4-y1)-L-alanines as Tridentate Ligands" Tetrahedron Letters, Elsevier, Amsterdam, NL LNDK-, DOI: 10.1016/S0040-4039(98)00711-4, vol. 39, No. 23, Jun. 4, 1998, pp. 3999-4002, XP004118795, ISSN: 0040-4039, Scheme 2; p. 4000.
Smyth, M.S., et al: "Enantioselective synthesis of N-boc and N-fmoc protected diethyl 4-phosphono(difluoromethyl)-L-phenylalanine; agents suitable for the solid-phase synthesis of peptides containing nonhydrolyzable analogues of 0-phosphotyrosine" Tetrahedron Letters, Elsevier, Amsterdam, NL LNDK-, DOI: 10.1016/S0040-4039(00)75835-7, vol. 35, No. 4, Jan. 1, 1994, pp. 551-554, XP026646224, ISSN: 0040-4039, Scheme 1; p. 552.
T. Carillo-Marquez, et al: "New routes to beta-cycloalylalanine derivatives using serine-derived organozinc reagents" Org.Biomol. Chem., vol. 3, Oct. 3, 2005, pp. 4117-4123, XP002577285, the whole document.
Balboni, G., et al., "Opioid pseudopeptides containing heteroaromatic or heteroaliphatic nuclei", *Peptides*., 2000, pp. 1663-1671, vol. 21, issue 10.
Schiller, P.W., et al., "Spontaneous degradation via diketopiperazine formation of peptides containing a tetrahydroisoquinoline-3-carboxylic acid residue in 2-position of the peptide sequence", *Intl. J. Pept. Protein Res.*, 1993, pp. 313-316, vol. 41, issue 3.
Wentland, M.P., et al., "8-Carboxamidocyclazocine analogues: redefining the structure-activity relationships of 2,6-methano-3-benzazocines", *Biorg. Med. Chem. Lett.*, 2001, pp. 623-626, vol. 11, issue 5.
Wentland, M.P., et al., "3-Carboxamido analogues of morphine and naltrexone: synthesis and opioid receptor binding properties", *Biorg. Med. Chem. Lett.*, 2001, pp. 1717-1721, vol. 11, issue 13.

*Primary Examiner* — Kristin Vajda

(74) *Attorney, Agent, or Firm* — Baker & Hostetler LLP

(57) ABSTRACT

The present invention is directed to a novel process for the preparation of protected L-alanine derivatives, useful as intermediates in the synthesis of compounds useful as mu/delta opioid modulators.

30 Claims, No Drawings

PROCESS FOR THE PREPARATION OF PROTECTED L-ALANINE DERIVATIVES

CROSS REFERENCE TO RELATED U.S. APPLICATION DATA

The present application is derived from and claims priority to provisional application U.S. Ser. No. 61/108,649, filed Oct. 27, 2008, which is herein incorporated by reference in its entirety.

FIELD OF THE INVENTION

The present invention is directed to a novel process for the preparation of protected L-alanine derivatives, useful as intermediates in the synthesis of compounds useful as mu/delta opioid modulators.

BACKGROUND OF THE INVENTION

The opioid receptors were identified in the mid-1970's, and were quickly categorized into three sub-sets of receptors (mu, delta and kappa). More recently the original three types of receptors have been further divided into sub-types. Also known is that the family of opioid receptors are members of the G-protein coupled receptor (GPCR) super-family. More physiologically pertinent are the well established facts that opioid receptors are found throughout the central and peripheral nervous system of many mammalian species, including humans, and that modulation of the respective receptors can elicit numerous, albeit different, biological effects, both desirable and undesirable (D. S. Fries, "Analgesics", in *Principles of Medicinal Chemistry*, 4th ed.; W. O. Foye, T. L. Lemke, and D. A. Williams, Eds.; Williams and Wilkins: Baltimore, Md., 1995; pp. 247-269; J. V. Aldrich, "Analgesics", *Burger's Medicinal Chemistry and Drug Discovery*, 5$^{th}$ Edition, Volume 3: Therapeutic Agents, John Wiley & Sons, Inc., 1996, pp. 321-441). In the most current literature, the likelihood of heterodimerization of the sub-classes of opioid receptors has been reported, with respective physiological responses yet undetermined (Pierre J. M. Riviere and Jean-Louis Junien, "Opioid receptors: Targets for new gastrointestinal drug development", Drug Development 2000, pp. 203-238).

Biological effects identified for opioid modulators have led to many useful medicinal agents. Most significant are the many centrally acting mu opioid agonist modulators marketed as analgesic agents to attenuate pain (e.g., morphine), as well as peripherally acting mu agonists to regulate motility (e.g., loperamide). Currently, clinical studies are continuing to evaluate medicinal utility of selective delta, mu, and kappa modulators, as well as compounds possessing combined sub-type modulation. It is envisioned such explorations may lead to agents with new utilities, or agents with minimized adverse side effects relative to currently available agents (examples of side effects for morphine includes constipation, respiratory depression, and addiction potential). Some new GI areas where selective or mixed opioid modulators are currently being evaluated includes potential treatment for various diarrheic syndromes, motility disorders (post-operative ileus, constipation), and visceral pain (post operative pain, irritable bowel syndrome, and inflammatory bowel disorders) (Pierre J. M. Riviere and Jean-Louis Junien, "Opioid receptors: Targets for new gastrointestinal drug development" Drug Development, 2000, pp. 203-238).

Around the same time the opioid receptors were identified, the enkephalins were identified as a set of endogenous opioid ligands (D. S. Fries, "Analgesics", in *Principles of Medicinal Chemistry*, 4th ed.; W. O. Foye; T. L. Lemke, and D. A. Williams, Eds.; Williams and Wilkins: Baltimore, Md., 1995; pp. 247-269). Schiller discovered that truncating the original pentapeptide enkephalins to simplified dipeptides yielded a series of compounds that maintained opioid activity (Schiller, P. WO 96/06855). However one potential drawback cited for such compounds is the likelihood of their inherent instability (P. W. Schiller et al., Int. J. Pept. Protein Res. 1993, 41 (3), pp. 313-316).

More recently, a series of opioid pseudopeptides containing heteroaromatic or heteroaliphatic nuclei were disclosed, however this series is reported showing a different functional profile than that described in the Schiller works. (L. H. Lazarus et al., *Peptides* 2000, 21, pp. 1663-1671)

Additionally, works around morphine related structures were reported by Wentland, et al, where carboxamido morphine derivatives and it's analogs were prepared (M. P. Wentland et al., *Biorg. Med. Chem. Letters* 2001, 11, pp. 1717-1721; M. P. Wentland et al., *Biorg. Med. Chem. Letters* 2001, 11, pp. 623-626). Wentland found that substitution for the phenol moiety of the morphine related structures with a primary carboxamide led anywhere from equal activities up to 40 fold reduced activities, depending on the opioid receptor and the carboxamide. It was also revealed that any additional N-substitutions on the carboxamide significantly diminished the desired binding activity.

Opioid receptor modulators, agonists or antagonists are useful in the treatment and prevention of various mammalian disease states, for example pain and gastrointestinal disorders, such as, diarrheic syndromes, motility disorders, including post-operative ileus and constipation, and visceral pain, including post-operative pain, irritable bowel syndrome, and inflammatory bowel disorders.

Breslin, H. J., et al., in U.S. Patent Publication 2005/0203143 A1, published Sep. 15, 2005, which is herein expressly incorporated by reference in its entirety, disclose opioid receptor modulators, pharmaceutical compositions including such modulators, and methods of treatment using such modulators. The present invention is directed to processes for the preparation of intermediates useful in the synthesis of the opioid receptor modulators as described in U.S. Patent Publication 2005/0203143 A1.

SUMMARY OF THE INVENTION

The present invention is directed to a process for the preparation of compounds of formula (I)

wherein
PG$^1$ is a nitrogen protecting group;
R$^0$ is selected from the group consisting of hydrogen, C$_{1-4}$alkyl and benzyl;
R$^6$ is selected from the group consisting of hydrogen and C$_{1-6}$alkyl;
R$^4$ is aryl or heteroaryl; wherein the aryl or heteroaryl is optionally substituted with one to five substituents independently selected from the group consisting of C$_{1-6}$alkyl, C$_{1-6}$alkoxy, arylC$_{1-6}$alkoxy, arylC$_{1-6}$alkylcarbonyloxy, heteroarylC$_{1-6}$alkylcarbonyloxy, heteroaryl, hydroxy, halogen, aminosulfonyl, formylamino, aminocarbonyl, C$_{1-6}$alkylaminocarbonyl, di(C$_{1-6}$alkyl)aminocarbonyl, heterocyclylcarbonyl, carboxy, and cyano; wherein the C$_{1-6}$alkyl is optionally substituted with amino, $C_{1-6}$alkylamino, or $(C_{1-6}alkyl)_2$amino; and wherein the aryl portion of aryl$C_{1-6}$alkylcarbonyloxy is optionally substituted with one to four substituents independently selected from the group consisting of $C_{1-6}$alkyl, $C_{1-6}$alkoxy, halogen, cyano, amino and hydroxy;

and pharmaceutically acceptable enantiomers, pharmaceutically acceptable diastereomers, pharmaceutically acceptable racemates and pharmaceutically acceptable salts thereof; comprising, consisting of and/or consisting essentially of

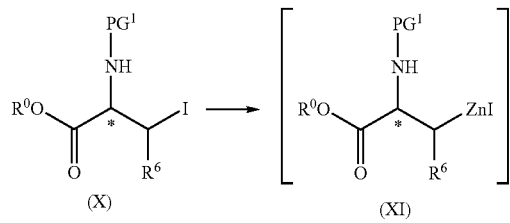

reacting a compound of formula (X), wherein $PG^1$ is a nitrogen protecting group, with zinc; in the presence of a source of iodine; in a first organic solvent or a mixture of organic solvents, wherein the first organic solvent is non-reactive to the source iodine; to yield the corresponding compound of formula (XI);

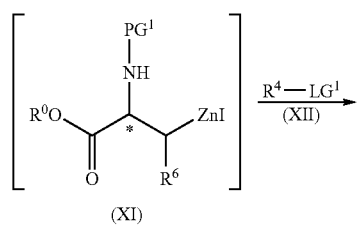

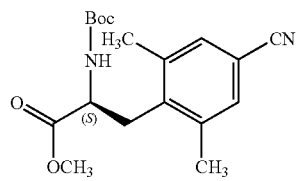

reacting the compound of formula (XI) with a compound of formula (XII), wherein $LG^1$ is a leaving group; in the presence of a palladium catalyst and phosphine ligand system; in a second organic solvent or a mixture of organic solvents; to yield the corresponding compound of formula (I).

The present invention is further directed to a process for the preparation of a compound of formula (I-B)

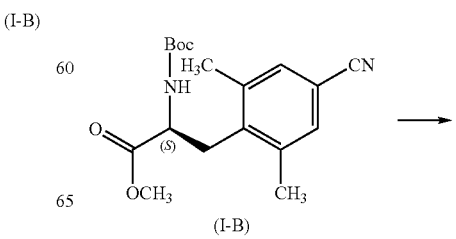

comprising, consisting of and/or consisting essentially of

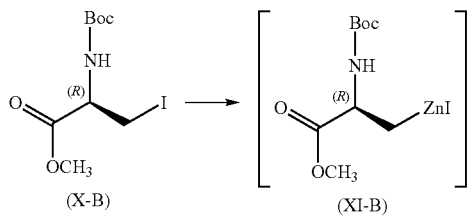

reacting a compound of formula (X-B) with zinc; in the presence of a source of iodine; in a first organic solvent or mixture a mixture of organic solvents, wherein the first organic solvent is non-reactive to the source iodine; to yield the corresponding compound of formula (XI-B);

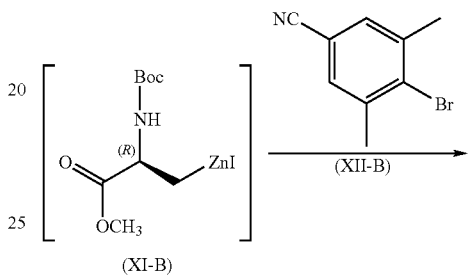

reacting the compound of formula (XI-B) with a compound of formula (XII-B); in the presence of a palladium catalyst and phosphine ligand system; in a second organic solvent or a mixture of organic solvents; to yield the corresponding compound of formula (I-B).

The present invention is further directed to a process for the preparation of a compound of formula (II-B)

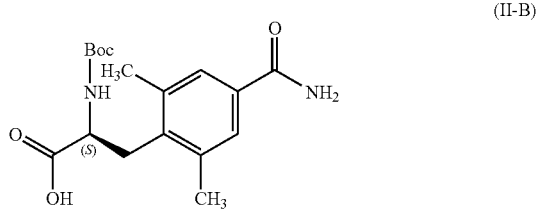

or a pharmaceutically acceptable salt thereof; comprising, consisting of and/or consisting essentially of -continued

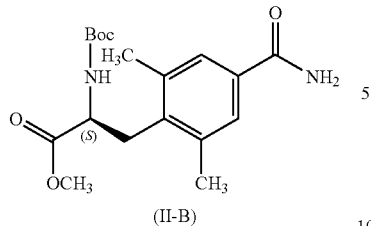

(II-B)

reacting a compound of formula (I-B) with an oxidizing agent; in the presence of an inorganic base; in a third organic solvent; to yield the corresponding compound of formula (II-B).

The present invention is further directed to a product prepared according to any of the processes described herein. Preferably, the compounds prepared according to the processes of the present invention are substantially pure.

DETAILED DESCRIPTION OF THE INVENTION

The present invention is directed to a novel process for the preparation of compounds of formula (I)

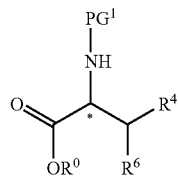

(I)

wherein $PG^1$, $R^0$, $R^4$ and $R^6$ are as herein defined, and pharmaceutically acceptable enantiomers, diastereomers, racemates and salts thereof. The compounds of formula (I) are useful as intermediates in the preparation of opiod receptor modulators as disclosed in U.S. Patent Publication US2005/0203143 A1, published Sep. 15, 2005, is which is hereby incorporated by reference in its entirety.

In an embodiment, the present invention is directed to a process for the preparation of compound of formula (I-A)

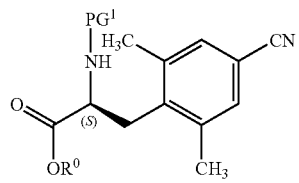

(I-A)

and further to a process for the preparation of a compound of formula (I-B)

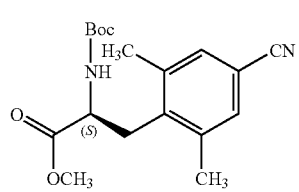

(I-B)

also known as (S)-2-tert-butoxycarbonylamino-3-(4-cyano-2,6-dimethyl-phenyl)-propionic acid methyl ester)

The present invention is further directed to a process for the preparation of a compound of formula (II-A)

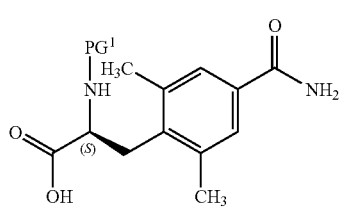

(II-A)

or a pharmaceutically acceptable salt thereof; and further to a process for the preparation of a compound of formula (II-B)

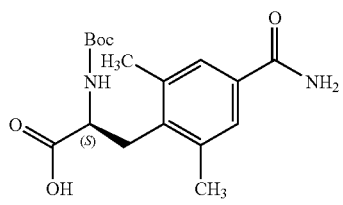

(II-B)

also known as (S)-2-tert-butoxycarbonylamino-3-(4-carbamoyl-2,6-dimethyl-phenyl)-propionic acid, or a pharmaceutically acceptable salt thereof.

In an embodiment of the present invention, $PG^1$ is selected from the group consisting of Boc and Cbz. In another embodiment of the present invention, $PG^1$ is Boc.

In an embodiment of the present invention, $R^0$ is selected from the group consisting of $C_{1-4}$alkyl and benzyl. In another embodiment of the present invention $R^0$ is selected from the group consisting of methyl, ethyl, isopropyl, t-butyl and benzyl. In another embodiment of the present invention, $R^0$ is methyl or benzyl. In another embodiment of the present invention $R^0$ is methyl. In another embodiment of the present invention, $R^0$ is other than hydrogen.

In an embodiment of the present invention, $R^6$ is selected from the group consisting of hydrogen and methyl. In another embodiment of the present invention, $R^6$ is hydrogen.

In an embodiment of the present invention, $R^4$ is selected from the group consisting of $C_{6-10}$aryl and a heteroaryl; wherein the heteroaryl is selected from the group consisting of furyl, thienyl, pyrrolyl, oxazolyl, thiazolyl, imidazolyl, pyrazolyl, pyridinyl, pyrimidinyl, pyrazinyl, indolyl, isoindolyl, indolinyl, benzofuryl, benzothienyl, benzimidazolyl, benzthiazolyl, benzoxazolyl, quinolizinyl, quinolinyl, isoquinolinyl and quinazolinyl; and wherein the $R^4$ is optionally substituted with one to three substituents independently selected from the group consisting of $C_{1-6}$alkyl (wherein the $C_{1-6}$alkyl is optionally substituted with amino, $C_{1-6}$alkylamino, or di($C_{1-6}$alkyl)amino); $C_{1-6}$alkoxy; phenyl$C_{1-6}$alkoxy; phenyl$C_{1-6}$alkylcarbonyloxy (wherein the $C_{1-6}$alkyl portion is optionally substituted with amino; and wherein the phenyl portion of phenyl$C_{1-6}$alkylcarbonyloxy is optionally substituted with $C_{1-6}$alkyl, $C_{1-6}$alkoxy, halogen, cyano, amino, or hydroxy); a non fused 5-membered-heteroaryl$C_{1-6}$ alkylcarbonyloxy; a non fused 5-membered-heteroaryl; hydroxy; halogen; aminosulfonyl; formylamino; aminocarbonyl; $C_{1-6}$alkylaminocarbonyl (wherein $C_{1-6}$alkyl portion is optionally substituted with amino, $C_{1-6}$alkylamino, or ($C_{1-6}$ alkyl)$_2$amino); di($C_{1-6}$alkyl)aminocarbonyl (wherein each $C_{1-6}$alkyl portion is optionally substituted with amino, $C_{1-6}$alkylamino, or ($C_{1-6}$alkyl)$_2$amino); heterocyclylcarbonyl (wherein the heterocyclyl is a 5-7 membered nitrogen-containing ring and wherein said heterocyclyl is attached to the carbonyl carbon via a nitrogen atom); carboxy; and cyano.

In another embodiment of the present invention, $R^4$ is $C_{6-10}$aryl optionally substituted with one to three substituents independently selected from the group consisting of $(C_{1-3})$alkyl, $(C_{1-6})$alkoxy, phenyl$(C_{1-6})$alkoxy; hydroxy; halogen; formylamino; aminocarbonyl; $C_{1-6}$alkylaminocarbonyl; $(C_{1-6}$alkyl$)_2$aminocarbonyl; heterocyclylcarbonyl wherein heterocyclyl is a 5-7 membered nitrogen-containing ring and said heterocyclyl is attached to the carbonyl carbon via a nitrogen atom; carboxy; and cyano; provided that no more than one of the substituents is formylamino, aminocarbonyl, $C_{1-6}$alkylaminocarbonyl, $(C_{1-6}$alkyl$)_2$aminocarbonyl, heterocyclylcarbonyl, hydroxy, carboxy, or a phenyl-containing substituent.

In another embodiment of the present invention $R^4$ is phenyl substituted with one to three substituents independently selected from the group consisting of $(C_{1-3})$alkyl, $(C_{1-3})$alkoxy, phenyl$(C_{1-3})$alkoxy, hydroxy, $C_{1-6}$alkylaminocarbonyl, and aminocarbonyl; provided that no more than one of the substituents is aminocarbonyl, $C_{1-6}$alkylaminocarbonyl, hydroxy, or a phenyl-containing substituent.

In another embodiment of the present invention, $R^4$ is phenyl substituted at the 4-position with hydroxy, $C_{1-3}$alkylaminocarbonyl, or aminocarbonyl, and further optionally substituted with one to two substituents independently selected from the group consisting of methyl, methoxy, and benzyloxy. In another embodiment of the present invention, $R^4$ is phenyl substituted at the 4-position with hydroxy, $C_{1-3}$alkylaminocarbonyl, or aminocarbonyl, and further optionally substituted with one to two methyl substituents. In another embodiment of the present invention, $R^4$ is phenyl substituted at the 4-position with hydroxy, $C_{1-3}$alkylaminocarbonyl, or aminocarbonyl, and further substituted at the 2- and 6-positions with methyl substituents.

In an embodiment, the present invention is directed to a process for the preparation of a compound of formula (I), wherein the stereo-center as indicated by the "*" is present in an enantiomeric excess of the (R) enantiomer. In another embodiment, the present invention s directed to a process for the preparation of a compound of formula (I), wherein the stereo-center as indicated by the "*" is present in an enantiomeric excess of the (S) enantiomer.

As used herein, unless otherwise noted, the term "alkyl" whether used alone or as part of a substituent group refers to straight and branched carbon chains having 1 to 8 carbon atoms or any number of carbon atoms within the end points of this range. The term "alkoxy" refers to an —Oalkyl substituent group, wherein alkyl is as defined supra. An alkyl and alkoxy chain may be substituted on a single carbon atom. In substituent groups with multiple alkyl groups such as di($C_{1-6}$alkyl)amino- the $C_{1-6}$alkyl groups of the dialkylamino may be the same or different.

The term "heterocyclyl" refers to a nonaromatic cyclic ring of 5 to 7 members in which 1 to 2 members are nitrogen, or a nonaromatic cyclic ring of 5 to 7 members in which zero, one or two members are nitrogen and up to two members are oxygen or sulfur; wherein, optionally, the ring contains zero to one unsaturated bonds, and, optionally, when the ring is of 6 or 7 members, it contains up to two unsaturated bonds. The term "heterocyclyl" includes a 5 to 7 membered monocyclic heterocyclic ring fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For compounds of the instant invention, the carbon atom ring members that form the heterocyclyl ring are fully saturated. Other compounds of the invention may have a partially saturated heterocyclyl ring. The term "heterocyclyl" also includes a 5 to 7 membered monocyclic heterocycle bridged to form bicyclic rings. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl, and piperazinyl.

The term "aryl" refers to an unsaturated, aromatic monocyclic ring of 6 carbon members or to an unsaturated, aromatic polycyclic ring of from 10 to 14 carbon members. Examples of such aryl rings include phenyl, naphthalenyl, or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include N, O, or S. In the case of 5 membered rings, the heteroaryl ring contains one member of N, O, or S and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. Optionally, the heteroaryl ring is fused to a benzene ring (benzo fused heteroaryl), a 5 or 6 membered heteroaryl ring (containing one of O, S, or N and, optionally, one additional nitrogen), a 5 to 7 membered cycloalkyl ring or a 5 to 7 membered heterocyclo ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl and pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl and quinazolinyl.

The term "arylalkyl" means an alkyl group substituted with an aryl group (e.g., benzyl and phenethyl). Similarly, the term "arylalkoxy" indicates an alkoxy group substituted with an aryl group (e.g., benzyloxy).

The term "halogen" refers to fluorine, chlorine, bromine and iodine. Substituents that are substituted with multiple halogens are substituted in a manner that provides compounds that are stable.

Whenever the term "alkyl" or "aryl" or either of their prefix roots appear in a name of a substituent (e.g., arylalkyl, alkylamino) it is to be interpreted as including those limitations given above for "alkyl" and "aryl." Designated numbers of carbon atoms (e.g., $C_1$-$C_6$) refers independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example $C_{1-6}$alkyl would include methyl, ethyl, propyl, butyl, pentyl and hexyl individually, as well as, sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

When a particular group is "substituted" (e.g., alkyl, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula

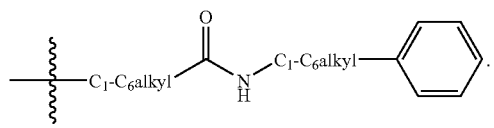

Abbreviations used in the specification, particularly the Schemes and Examples, are as follows:

| | |
|---|---|
| AcCN = | Acetonitrile |
| Boc, or BOC = | tert-Butoxycarbonyl |
| Cbz = | Benzyloxycarbonyl |
| DMA or DMAc = | Dimethylacetamide |
| DMF = | N,N-Dimethylformamide |
| DMSO = | Dimethylsulfoxide |
| EtOAc = | Ethyl acetate |
| HPLC = | High Pressure Liquid Chromatography |
| MeOH = | Methanol |
| 2-Me-THF = | 2-methyl-tetrahydrofuran |

| | |
|---|---|
| NMP = | N-Methyl-pyrrolidone |
| Pd$_2$(dba)$_3$ = | Tris(dibenzylidene acetone)dipalladium(0) |
| Pd(PPh$_3$)$_4$ = | Tetrakistriphenylphosphine palladium (0) |
| Pd(PPh$_3$)$_2$Cl$_2$ = | Bis(triphenylphosphine)palladium (II) chloride |
| P(o-tol)$_3$ = | Tri-(o-tolyl) phosphine |
| PPh$_3$ = | Triphenyl phosphine |
| THF = | Tetrahydrofuran |

As used herein, unless otherwise noted, the term "substantially pure compound" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is prepared as a substantially pure compound. In an embodiment of the present invention, the compound of formula (I-A) is prepared as a substantially pure compound. In another embodiment of the present invention, the compound of formula (I-B) is prepared as a substantially pure compound. In an embodiment of the present invention, the compound of formula (II-A) is prepared as a substantially pure compound. In another embodiment of the present invention, the compound of formula (II-B) is prepared as a substantially pure compound.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is prepared in a form which is substantially free of corresponding salt form(s). In an embodiment of the present invention, the compound of formula (II-A) is prepared in a form that is substantially free of corresponding salt form(s). In another embodiment of the present invention, the compound of formula (II-B) is prepared in a form that is substantially free of corresponding salt form(s).

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g., base, solvent, etc.) is recited in more than one step of a process, the individual reagents are independently selected for each reaction step and may be the same of different from each other. For example, where two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e., the product of the first of the two consecutive reaction or process steps), then the first and second reaction or process steps may be run in the same solvent or solvent system; or, alternatively, may be run in different solvents or solvent systems following solvent exchange, which may be completed according to known methods.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to Cl, Br, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" refers to a group that may be attached to a nitrogen atom to protect the nitrogen atom from participating in a reaction and that may be readily removed following the reaction. Suitable nitrogen protecting groups include carbamates—groups of the formula —C(O)O—R wherein R is, for example, methyl, ethyl, t-butyl, benzyl, phenylethyl, $CH_2=CH-CH_2-$, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

One skilled in the art will recognize that where a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as, the formation of diastereomeric pairs by salt formation with an optically active acid, such as, (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha-obs]/[\alpha-max]) \times 100.$$

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts that may, for example, be formed by mixing a solution of the compound with a solution of a pharmaceutically acceptable acid, such as, hydrochloric acid, sulfuric acid, fumaric acid, maleic acid, succinic acid, acetic acid, benzoic acid, citric acid, tartaric acid, carbonic acid and phosphoric acid. Furthermore, where the compounds of the invention carry an acidic moiety, suitable pharmaceutically acceptable salts thereof may include alkali metal salts, e.g., sodium and potassium salts; alkaline earth metal salts, e.g., calcium and magnesium salts; and salts formed with suitable organic ligands, e.g., quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids that may be used in the preparation of pharmaceutically acceptable salts include: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid, and undecylenic acid.

Representative bases that may be used in the preparation of pharmaceutically acceptable salts include: bases including, ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine, and zinc hydroxide.

The present invention is directed to a process for the preparation of compounds of formula (I) as described in more detail in Scheme 1 below.

Scheme 1

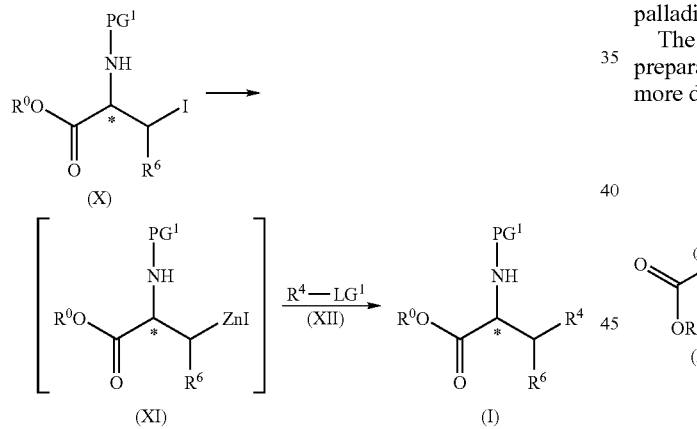

Accordingly, a suitably substituted compound of formula (X), a known compound or compound prepared by known methods, wherein $PG^1$ is a suitably selected nitrogen protecting group such as Boc, Cbz, and the like, preferably Boc; is reacted with zinc, preferably zinc powder; wherein the zinc is preferably present in an amount in the range of from about 0.5 to about 3.0 molar equivalents, more preferably present in an amount in the range of from about 0.5 to about 1.5 molar equivalents, more preferably about 1.1 molar equivalents; in the presence of a source of iodine, preferably iodine; wherein the source of iodine is preferably present in an amount in the range of from about 0.1 to about 1.0 molar equivalents, more preferably in an amount in the range of from about 0.1 to about 0.5 molar equivalents, more preferably about 0.3 molar equivalents, more preferably in a catalytic amount sufficient to activate the zinc; in a first organic solvent or mixture thereof, wherein the first organic solvent is non-reactive to the source iodine, such as, DMAc, a mixture of DMAc and 2-methyl-THF, THF, toluene, DMF, and the like, more preferably DMAc; preferably at a temperature in the range of from about −20° C. to about 10° C., more preferably at a temperature of less than about 10° C., more preferably at about −8° C.; to yield the corresponding compound of formula (XI). Preferably, the compound of formula (XI) is not isolated. Preferably, the zinc and source of iodine are mixed prior to addition to the compound of formula (X), to activate the zinc.

The compound of formula (XI) is reacted with a suitably substituted compound of formula (XII), wherein $LG^1$ is a suitably selected leaving group such as, Cl, Br, I, and the like, preferably Br; wherein the compound of formula (XII) is preferably present in an amount in the range of from about 0.1 to about 3.0 molar equivalents, more preferably in an amount in the range of from about 0.25 to about 1.0 molar equivalents, more preferably in an amount in the range of from about 0.5 to about 1.1 molar equivalents; in the presence of a palladium catalyst and phosphine ligand system such as $Pd_2(dba)_3$ in combination with $P(o\text{-}tol)_3$, palladium chloride in combination with $PPh_3$, $Pd(PPh_3)_2Cl_2$, $Pd(PPh_3)_4$, and the like, more preferably $Pd_2(dba)_3$ in combination with $P(o\text{-}tol)_3$, wherein the palladium catalyst and phosphine ligand system is preferably present in a catalytic amount; in a second organic solvent or mixture thereof such as, DMAc, a mixture of DMAc and 2-methyl-THF, THF, DMF, toluene, and the like, more preferably DMAc; preferably in the same solvent as used in the previous step; preferably at a temperature in the range of from about 50° C. to about 100° C., more preferably at about 80° C.; to yield the corresponding compound of formula (I). Preferably, the compound of formula (XI) is added to a mixture of the compound of formula (XII), the palladium catalyst and the phosphine agent.

The present invention is further directed to a process for the preparation of a compound of formula (I-A) as described in more detail in Scheme 2, below.

Scheme 2

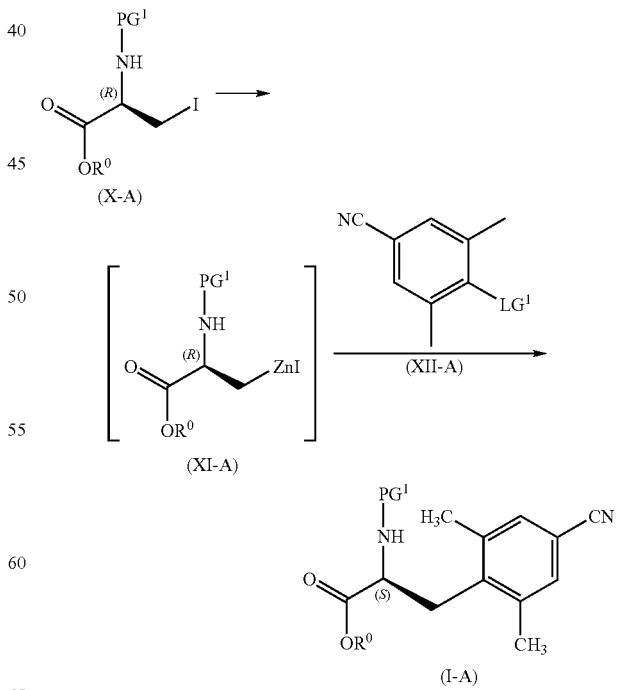

Accordingly, a suitably substituted compound of formula (X-A), a known compound or compound prepared by known methods, wherein PG¹ is a suitably selected nitrogen protecting group such as Boc, Cbz, and the like, preferably Boc; is reacted with zinc, preferably zinc powder; wherein the zinc is preferably present in an amount in the range of from about 0.5 to about 3.0 molar equivalents, more preferably present in an amount in the range of from about 0.5 to about 1.5 molar equivalents, more preferably about 1.1 molar equivalents; in the presence of a source of iodine, preferably iodine; wherein the source of iodine is preferably present in an amount in the range of from about 0.1 to about 1.0 molar equivalents, more preferably in an amount in the range of from about 0.1 to about 0.5 molar equivalents, more preferably about 0.3 molar equivalents, more preferably in a catalytic amount sufficient to activate the zinc; in a first organic solvent or mixture thereof, wherein the first organic solvent is non-reactive to the source iodine, such as, DMAc, a mixture of DMAc and 2-methyl-THF, THF, toluene, DMF, and the like, more preferably DMAc; preferably at a temperature in the range of from about −20° C. to about 10° C., more preferably at a temperature of less than about 10° C., more preferably at about −8° C.; to yield the corresponding compound of formula (XI-A). Preferably, the compound of formula (XI-A) is not isolated. Preferably, the zinc and source of iodine are mixed prior to addition to the compound of formula (V-A), to activate the zinc.

The compound of formula (XI-A) is reacted with a suitably substituted compound of formula (XII-A), wherein LG¹ is a suitably selected leaving group, such as, Cl, Br, I, and the like, preferably Br; wherein the compound of formula (XII-A) is preferably present in an amount in the range of from about 0.1 to about 3.0 molar equivalents, more preferably in an amount in the range of from about 0.25 to about 1.0 molar equivalents, more preferably in an amount in the range of from about 0.5 to about 1.1 molar equivalents; in the presence of a palladium catalyst and phosphine ligand system such as Pd₂(dba)₃ in combination with P(o-tol)₃, palladium chloride in combination with PPh₃, Pd(PPh₃)₂Cl₂, Pd(PPh₃)₄, and the like, more preferably Pd₂(dba)₃ in combination with P(o-tol)₃, wherein the palladium catalyst and phosphine ligand system is preferably present in a catalytic amount; in a second organic solvent or mixture thereof, such as, DMAc, a mixture of DMAc and 2-methyl-THF, THF, DMF, toluene, and the like, more preferably DMAc; preferably in the same solvent as used in the previous step; preferably at a temperature in the range of from about 50° C. to about 100° C., more preferably at about 80° C.; to yield the corresponding compound of formula (I-A). Preferably, the compound of formula (XI-A) is added to a mixture of the compound of formula (XII-A), the palladium catalyst and the phosphine agent.

The present invention is further directed to a process for the preparation of a compound of formula (I-B), as described in more detail in Scheme 3, Scheme 3

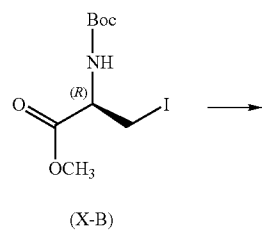

(X-B)

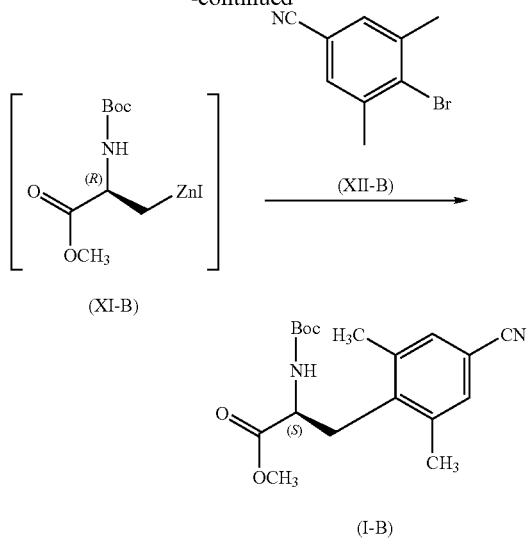

Accordingly, a suitably substituted compound of formula (X-B), a known compound or compound prepared by known methods, is reacted with zinc, preferably zinc powder; wherein the zinc is preferably present in an amount in the range of from about 0.5 to about 3.0 molar equivalents, more preferably present in an amount in the range of from about 0.5 to about 1.5 molar equivalents, more preferably about 1.1 molar equivalents; in the presence of a source of iodine, preferably iodine; wherein the source of iodine is preferably present in an amount in the range of from about 0.1 to about 1.0 molar equivalents, more preferably in an amount in the range of from about 0.1 to about 0.5 molar equivalents, more preferably about 0.3 molar equivalents, more preferably in a catalytic amount sufficient to activate the zinc; in a first organic solvent or mixture thereof, wherein the first organic solvent is non-reactive to the source iodine, such as, DMAc, a mixture of DMAc and 2-methyl-THF, THF, toluene, DMF, and the like, more preferably DMAc; preferably at a temperature in the range of from about −20° C. to about 10° C., more preferably at a temperature of less than about 10° C., more preferably at about −8° C.; to yield the corresponding compound of formula (XI-B). Preferably, the compound of formula (XI-B) is not isolated. Preferably, the zinc and source of iodine are mixed prior to addition to the compound of formula (V-B), to activate the zinc.

The compound of formula (XI-B) is reacted with a suitably substituted compound of formula (XII-B), wherein the compound of formula (XII-B) is preferably present in an amount in the range of from about 0.1 to about 3.0 molar equivalents, more preferably in an amount in the range of from about 0.25 to about 1.0 molar equivalents, more preferably in an amount in the range of from about 0.5 to about 1.1 molar equivalents; in the presence of a palladium catalyst and phosphine ligand system such as Pd₂(dba)₃ in combination with P(o-tol)₃, palladium chloride in combination with PPh₃, Pd(PPh₃)₂Cl₂, Pd(PPh₃)₄, and the like, more preferably Pd₂(dba)₃ in combination with P(o-tol)₃, wherein the palladium catalyst and phosphine ligand system is preferably present in a catalytic amount; in a second organic solvent or mixture thereof, such as, DMAc, a mixture of DMAc and 2-methyl-THF, THF, DMF, toluene, and the like, more preferably DMAc; preferably in the same solvent as used in the previous step; preferably at a temperature in the range of from about 50° C. to about 100° C., more preferably at about 80° C.; to yield the corresponding compound of formula (I-B). Preferably, the compound of formula (XI-B) is added to a mixture of the compound of formula (XII-B), the palladium catalyst and the phosphine agent.

The present invention is further directed to a process for the preparation of a compound of formula (II-A), as described in more detail in Scheme 4, below.

Scheme 4

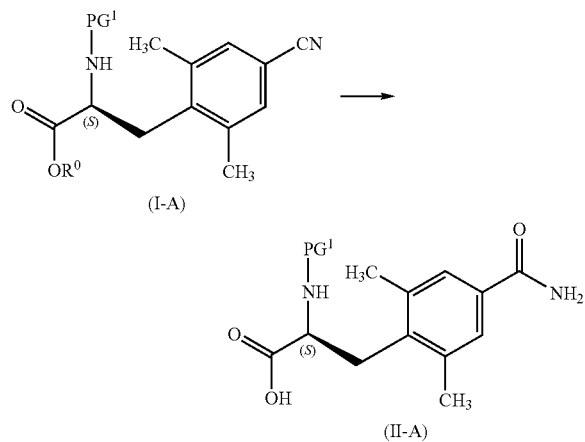

Accordingly, a suitably substituted compound of formula (I-A), wherein $R^0$ is preferably other than hydrogen, and wherein $PG^1$ is a suitably selected nitrogen protecting group such as Boc, Cbz, and the like, preferably $PG^1$ is Boc, is reacted with a suitably selected oxidizing agent, such as, hydrogen peroxide, LiOH, LiOOH, and the like, preferably 30% hydrogen peroxide; wherein the oxidizing agent is preferably present in an excess amount; in the presence of an inorganic base, such as, potassium carbonate, sodium carbonate, sodium percarbonate, and the like, preferably potassium carbonate; wherein the inorganic base is preferably present in an amount in the range of from about 1.0 to about 3.0 molar equivalent, more preferably in an amount of about 1.6 molar equivalents; in a third organic solvent, such as, DMSO, DMF, DMAc, NMP, and the like, preferably DMSO; at a temperature in the range of from about room temperature to about 60° C., preferably at about 45° C.; to yield the corresponding compound of formula (II-A).

In an embodiment, the present invention is directed to a process for the preparation of a compound of formula (II-B), as described in more detail in Scheme 5, below.

Scheme 5

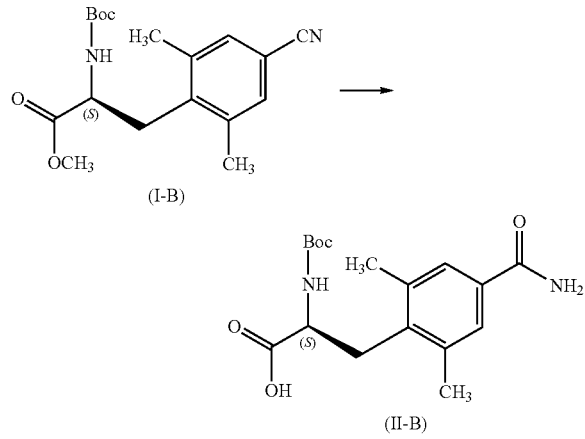

Accordingly, a suitably substituted compound of formula (I-B), is reacted with a suitably selected oxidizing agent, such as, hydrogen peroxide, LiOH, LiOOH, and the like, preferably about 30% hydrogen peroxide; wherein the oxidizing agent is preferably present in an excess amount, more preferably wherein the oxidizing agent is an excess amount of about 30% hydrogen peroxide; in the presence of an inorganic base, such as, potassium carbonate, sodium carbonate, sodium percarbonate, and the like, preferably potassium carbonate; wherein the inorganic base is preferably present in an amount in the range of from about 1.0 to about 3.0 molar equivalent, more preferably in an amount of about 1.6 molar equivalents; in a third organic solvent such as DMSO, DMF, DMAc, NMP, and the like, preferably DMSO; at a temperature in the range of from about room temperature to about 60° C., preferably at about 45° C.; to yield the corresponding compound of formula (II-B).

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

Preparation of 2-tert-Butoxycarbonylamino-3-(4-carbamoyl-2,6-dimethyl-phenyl)-propionic acid methyl ester

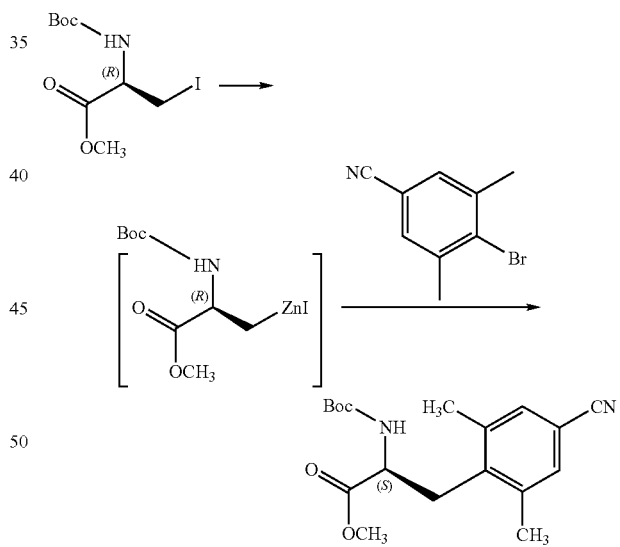

STEP A

Dry DMAc (300 mL), 2-Me-THF (150 mL), $I_2$ (25.4 g, 0.10 mol) and zinc powder (294.3 g, 4.5 mol), were added under nitrogen to a 3 L four-necked round bottom flask equipped with an addition funnel, mechanical stirrer, heating mantel, condenser and thermocouple. The resulting slurry was stirred until the red color of $I_2$ disappeared (about 2 minutes). During the addition, a temperature increase was observed (from 23° C. to 43° C.). The resulting mixture was cooled down using an ice/NaCl bath to about −5° C. to −2° C.

While at this temperature, a solution of Boc-6-iodo-alanine-OCH₃ (also known as 2-tert-butoxycarbonylamino-3-iodo-propionic acid methyl ester, 658.3 g, 2.0 mol) in a mixture of DMAc (250 mL) and 2-Me-THF (500 mL) was added slowly over a period of 2 hours. The temperature of the resulting mixture was maintained below 10° C. and the mixture aged for a period of about 1-2 hours in the ice bath, then warmed to about 15° C. to yield a mixture. The resulting cooled mixture was used in the next step without further manipulation.

STEP B

4-Iodo-3,5-dimethyl-benzamide (275 g, 1.0 mol), 2-Me-THF (500 mL) and DMA (200 mL), were added to a 5 L four-necked round bottom flask equipped with mechanical stirrer, heating mantel, condenser, thermocouple and nitrogen inlet. P(o-tol)₃ (24.5 g, 0.08 mol) and Pd₂(dba)₃ (36.6 g, 0.04 mol) were added to the suspension and the resulting slurry was heated to 45-50° C. While at this temperature, the mixture prepared in STEP A was added by cannula over a period of about 1.5-2 hours. The resulting mixture was cooled to ambient temperature. Silica (275 g) was added and the slurry stirred for about 30 minutes. The silica pad was washed with 2-Me-THF (3×500 mL) and EtOAc (3×1 L). The resulting solution was quenched with 2 L of 1.0N aqueous HCl and the layers were separated. The acidic layer was back extracted with EtOAc (2×1 L). The organic layer was concentrated to about 5.0 L in a rotoevaporator and rinsed with water (3×1 L), and with 50% brine (2.0 L). The solvents were removed by rotoevaporator to yield an off-white solid.

The title compound was crystallized from EtOAc (2 L) and heptane (2 L) as follows. After 16 hours the resulting mixture was cooled in an ice bath for 2 hours and more heptane (500 mL) was added to complete the precipitation. The solid was filtered and dried in a vacuum oven at 55° C. for 48 hours to yield the title compound as a white solid.

Example 2

Preparation of (S)-2-tert-Butoxycarbonylamino-3-(4-cyano-2,6-dimethyl-phenyl)-propionic acid methyl ester

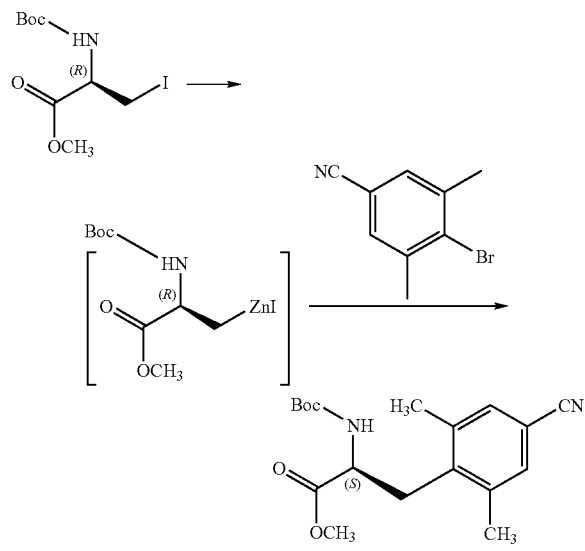

A 50 mL three-necked round bottom flask equipped with an addition funnel, magnetic stirrer, heating mantel, and thermocouple was charged under nitrogen dry DMAc (2 mL), I₂ (38.1 mg, 0.15 mmol) and zinc powder activated (washed with 10% HCl, rinsed with H₂O and acetone) (393 mg, 6 mmol). The resulting mixture was stirred at 23° C. until the red color of I₂ disappeared (2 minutes). A solution of Boc-β-iodo-L-alanine methyl ester (1 g, 3 mmol) in DMAc (2 mL) was added slowly, (temperature change from 21° C. to 29° C.) and the resulting mixture was stirred at 80° C. for 0.5-1 hour, then co cooled to 35° C. To the resulting mixture were added, successively, 4-bromo-3,5-dimethyl-benzonitrile (315 mg, 1.5 mmol) in DMAc (6 mL), P(o-tol)₃ (36.5 mg, 0.12 mmol) and Pd₂(dba)₃ (55 mg, 0.06 mmol). The resulting mixture was heated to 70° C., with stirring for 1 hour, then cooled to ambient temperature. The resulting mixture was diluted with EtOAc (15 mL) and filtered with STAND SUPER-CEL 815520. The EtOAc solution was quenched with 1 N HCl (40 mL) and extracted with ethyl acetate (20 mL). The combined organic phases were washed with H₂O (2×50 mL) and then with 50% brine, dried over Na₂SO₄, filtered and evaporated to dryness in vacuo to yield a brown solid. The title compound was crystallized from EtOAc (5 mL) and heptane (40 mL) to yield a white solid.

Example 3

Preparation of (S)-2-tert-Butoxycarbonylamino-3-(4-cyano-2,6-dimethyl-phenyl)-propionic acid methyl ester

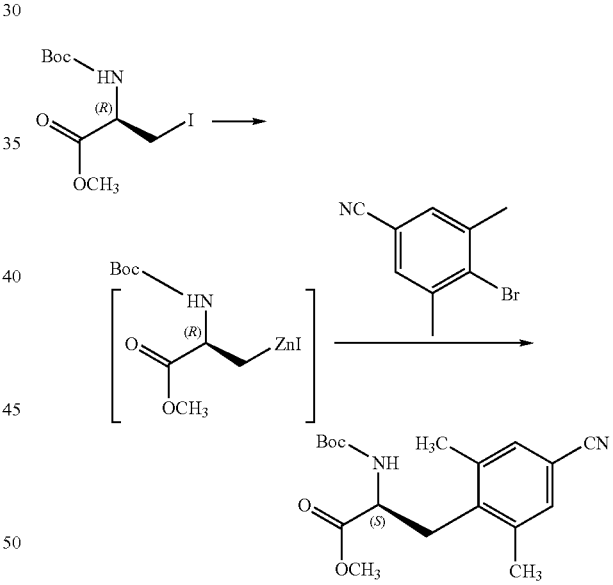

STEP A: Boc-β-iodo-Alanine methyl ester

A 2 L four-necked round-bottomed flask equipped with a nitrogen inlet, a mechanical stirrer, an addition funnel and a thermocouple was charged with anhydrous DMAc (500 mL) and iodine (16.8 g, 0.06 mol) to yield a red solution. To the stirred solution was then added zinc powder (143.9 g, 2.2 mol). The red color of the resulting mixture was observed to disappear in about 2 minutes, and an exotherm (22° C. to about 36° C.) was observed. The resulting mixture was cooled to −8° C. and then a solution of N-(tert-butoxycarbonyl)-3-iodo-L-alanine methyl ester (658 g, 2.0 mol) in anhydrous DMAc (500 mL) was added slowly over about 2 hours, maintaining the mixture temperature at below about 10° C., without stirring. The resulting cooled mixture was used in the next step without further manipulation.

STEP B: (S)-2-tert-Butoxycarbonylamino-3-(4-cyano-2,6-dimethyl-phenyl)-propionic acid methyl ester A 5 L three-necked round-bottomed flask equipped with a nitrogen inlet, a mechanical stirred, an addition funnel and a thermocouple was charged with 4-bromo-3,5-dimethyl-benzonitrile (210 g, 1.0 mol) and DMAc (750 ml). The resulting suspension was stirred and heated to 35° C. to dissolve the solids. To the resulting mixture was then added P(o-tol)$_3$ (6.0 g, 0.02 mol), Pd$_2$(dba)$_3$ (9.2 g, 0.01 mol) and the resulting mixture heated to about 75-80° C. The cooled mixture prepared in STEP A above was added by cannula to the reaction mixture at a rate which maintained the temperature at about 75-80° C. (about 2 hours). The resulting suspension was cooled to ambient temperature, then aged overnight with moderate agitation. The resulting suspension was then heated to about 35-40° C., filtered with silica (540 g). The silica bed was washed with DMAc (400 mL×2), the combined DMAc solutions cooled to about 0-5° C. and then added slowly to a mixture of ice and deionized water. The resulting mixture was maintained cold for 2 hours, over which time a white solid was observed to precipitate. The resulting mixture was then warmed to ambient temperature and aged overnight. The solid precipitate was cooled by vacuum filtration using a Buchner funnel. The filter cake was rinsed with deionized water (1 L×3), air dried overnight, then dried in a vacuum oven overnight. MeOH (1 L) was added to the solid and the resulting slurry was cooled to about 0-5° C., then aged at this temperature for 1 hour, with stirring. The solid was collected by filtration, washed with cold methanol (400 mL) and dried in a vacuum oven at 45° C. to yield the title compound as an off-white solid.

Example 4

Preparation of 4-Bromo-3,5-dimethyl-benzonitrile

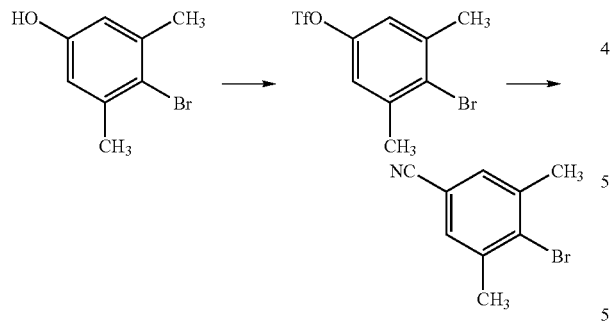

4-Bromo-3,5-dimethylphenol (50.0 g, 0.25 mol from Aldrich 99%) and pyridine (250 mL), were added to a 3 necked, 2.0 L round bottomed flask equipped with addition funnel, mechanical stirrer and thermocouple. The resulting solution was cooled to 0° C. and trifluoromethanesulfonic anhydride (triflic anhydride) (80.5 g, 0.285 mol from Aldrich 99%) was added dropwise over a period of 2 hours. After the addition, the resulting mixture was maintained at 0° C. for 15 minutes, then left overnight at room temperature. After 16 hours the resulting mixture was cooled down in an ice bath and quenched with H$_2$O (1.7 L), and EtOAc (1.7 L). The layers of the resulting biphasic mixture were separated and the organic layer was treated with HCl 2N (2×1.0 L), then rinsed once with water (1.0 L) and once with 50% brine. The organic layer was dried over Na$_2$SO$_4$, then concentrated to dryness by rotavapor to yield trifluoromethanesulfonic acid 4-bromo-3,5-dimethyl-phenyl ester as thick oil.

Trifluoro-methanesulfonic acid 4-bromo-3,5-dimethyl-phenyl ester (79.8 g, 0.24 mol) and AcCN (500 mL) were added to a 3 necked, 2.0 L round bottom flask equipped with mechanical stirrer, nitrogen inlet adapter, heating mantle and thermocouple. To the resulting solution were then added Pd(PPh$_3$)$_4$ (27.7 g, 0.024 mol), CuI (9.2 g, 0.048 mol) and Zn(CN)$_2$ (79.8 g, 0.24 mol). The resulting mixture was stirred for 45 minutes at 50° C., DMAc (150 mL) was added and the temperature was increased to 80-88° C. and the mixture aged at this temperature overnight. The resulting mixture was cooled to ambient temperature, diluted with EtOAc (200 mL), and filtered with STAND SUPER-CEL 815520. The SUPER-CEL cake was rinsed with EtOAc (200 mL×6). The EtOAc solutions were combined and quenched with a 4:1:4 mixture of saturated NH$_4$Cl: concentrated NH$_4$OH:H$_2$O (240 mL:60 mL:240 mL). The layers were separated and the organic layer was rinsed once with water (500 mL) and once with brine (500 mL), then concentrated to dryness in vacuo to yield a red thick oil. The title compound was crystallized from EtOAc (135 mL) and heptane (500 mL) to yield white-yellowish crystal.

Example 5

Preparation of (S)-2-tert-Butoxycarbonylamino-3-(4-carbamoyl-2,6-dimethyl-phenyl)-propionic acid

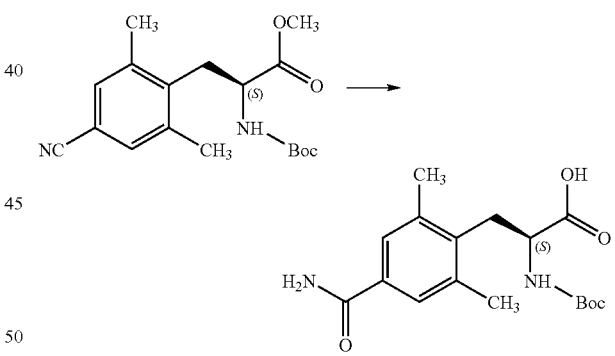

A 50 mL three-necked round bottom flask equipped with magnetic stirrer, and thermocouple was charged under nitrogen with (S)-2-tert-butoxycarbonylamino-3-(4-cyano-2,6-dimethyl-phenyl)-propionic acid methyl ester (166.2 mg, 0.5 mmol), DMSO (5.0 mL), and K$_2$CO$_3$ (75 mg, 0.5 mmol) and the resulting mixture cooled in an ice bath. To the resulting mixture was then added 30% H$_2$O$_2$ (110 µl), dropwise via a syringe. The resulting mixture was then allowed to warm up to ambient temperature, with the solids observed to dissolve to yield a clear solution. After stirring for about 2 hours at 45-50° C., water (10 mL) was added, cooling was applied, and a precipitated product isolated by filtration. The isolated white solid was washed with water (2×25 mL), then dried for 24 hours on high vacuum pump to yield the title compound as a white solid.

Example 6

Preparation of 2-tert-Butoxycarbonylamino-3-(4-carbamoyl-2,6-dimethyl-phenyl)-propionic acid

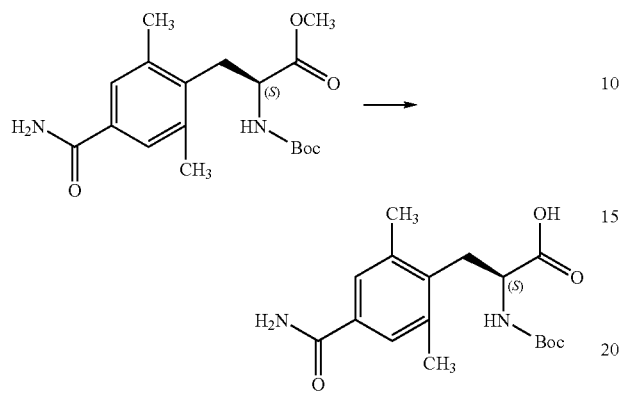

2-tert-Butoxycarbonylamino-3-(4-carbamoyl-2,6-dimethyl-phenyl)-propionic acid methyl ester (250 g, 0.713 mol), DMSO (750 mL) and 30% $H_2O_2$ (250 mL), were added to a 5 L three-necked round bottom flask equipped with addition funnel, mechanical stirrer, heating mantel, reflux condenser, thermocouple and nitrogen inlet. Potassium carbonate (158 g, 1.14 mol, 1.6 eq) was dissolved in water (750 mL) and added dropwise over 30 minutes. During the addition, a temperature increase was observed (from 23° C. to 34° C.). The resulting mixture was warmed up to about 42-45° C. and the progress of the reaction monitored by HPLC. After 3 hours, to the warm mixture was added activated carbon (ECOSORB-941) (37.5 g, 15% by weight). The resulting slurry was refluxed for 1 hour, and then filtered hot through CELITE®. The CELITE® pad was rinsed with $H_2O$ (1.5 L). The resulting mixture was cooled to about 10° C. and quenched with 2.0N HCl (pH 2, 1.22 L), to yield a mixture comprising a white solid precipitated. The mixture was aged under agitation for a period of about 4 hours in an ice bath and then filtered and dried for 48 hours in a vacuum oven to yield the title compound as a white crystalline solid.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for the preparation of a compound of formula (I)

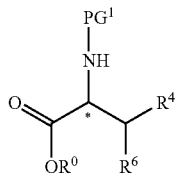

wherein
  $PG^1$ is a nitrogen protecting group;
  $R^0$ is selected from the group consisting of hydrogen, $C_{1-4}$-alkyl and benzyl;
  $R^6$ is selected from the group consisting of hydrogen and $C_{1-6}$alkyl;
  $R^4$ is aryl or heteroaryl; wherein the aryl or heteroaryl is optionally substituted with one to five substituents independently selected from the group consisting of $C_{1-6}$alkyl, $C_{1-6}$alkoxy, aryl$C_{1-6}$alkoxy, aryl$C_{1-6}$alkylcarbonyloxy, heteroaryl$C_{1-6}$alkylcarbonyloxy, heteroaryl, hydroxy, halogen, aminosulfonyl, formylamino, aminocarbonyl, $C_{1-6}$alkylaminocarbonyl, di($C_{1-6}$alkyl)aminocarbonyl, heterocyclylcarbonyl, carboxy, and cyano; wherein the $C_{1-6}$alkyl is optionally substituted with amino, $C_{1-6}$alkylamino, or ($C_{1-6}$alkyl)$_2$amino; and wherein the aryl portion of aryl$C_{1-6}$alkylcarbonyloxy is optionally substituted with one to four substituents independently selected from the group consisting of $C_{1-6}$alkyl, $C_{1-6}$alkoxy, halogen, cyano, amino and hydroxy;
  and pharmaceutically acceptable enantiomers, pharmaceutically acceptable diastereomers, pharmaceutically acceptable racemates and pharmaceutically acceptable salt thereof;
comprising

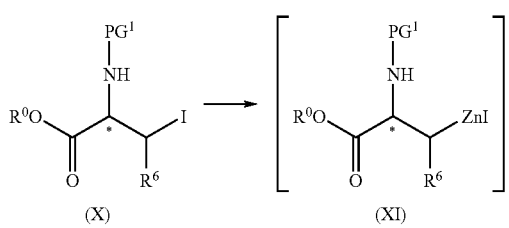

reacting a compound of formula (X), wherein $PG^1$ is a nitrogen protecting group, with zinc; in the presence of a source of iodine; in a first organic solvent, or a mixture of organic solvents wherein the first organic solvent is non-reactive to the source iodine; to yield the corresponding compound of formula (XI);

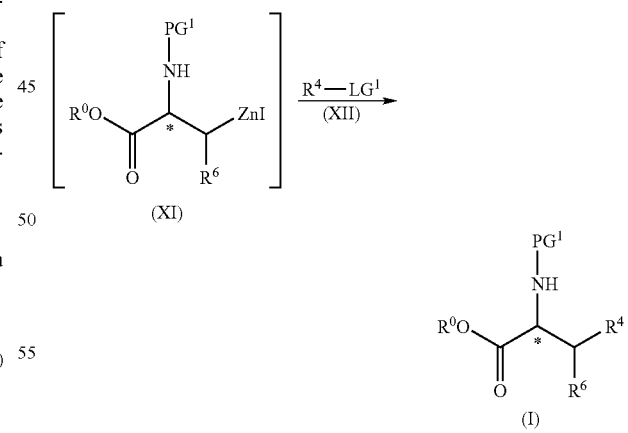

reacting the compound of formula (XI) with a compound of formula (XII), wherein $LG^1$ is a leaving group; in the presence of a palladium catalyst and phosphine ligand system; in a second organic solvent or a mixture of organic solvents; to yield the corresponding compound of formula (I).

2. The process as in claim 1 wherein $PG^1$ is Boc.

3. The process as in claim 1, wherein $R^0$ is methyl.

4. The process as in claim 1, wherein the zinc is zinc powder.

5. The process as in claim 4, wherein the zinc powder is present in an amount in the range of from about 0.5 to about 1.5 molar equivalents.

6. The process as in claim 1, wherein the source of iodine is iodine.

7. The process as in claim 6, wherein the iodine is present in an amount in the range of from about 0.1 to about 0.5 molar equivalents.

8. The process as in claim 1, wherein the first organic solvent is DMAc.

9. The process as in claim 1, wherein the compound of formula (X) is reacted with the zinc at a temperature of less than about 10° C.

10. The process as in claim 1, wherein the zinc and source of iodine are mixed prior to addition to the compound of formula (X).

11. The process as in claim 1, wherein LG$^1$ is bromo.

12. The process as in claim 1, wherein the compound of formula (XII) is present in an amount in the range of from about 0.25 to about 1.0 molar equivalents.

13. The process as in claim 1, wherein the palladium catalyst and phosphine ligand system is a combination of Pd$_2$(dba)$_3$ and P(o-tol)$_3$.

14. The process as in claim 1, wherein the second organic solvent is DMAc.

15. The process as in claim 1, wherein the compound of formula (X) is reacted with the compound of formula (XII) at a temperature in the range of from about 50° C. to about 100° C.

16. The process as in claim 1, wherein the compound of formula (XI) is added to a mixture of the compound of formula (XII), the palladium catalyst and phosphine ligand system.

17. A process for the preparation of a compound of formula (I-B)

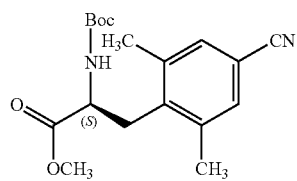

comprising

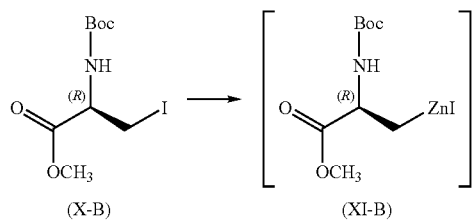

reacting a compound of formula (X-B) with zinc; in the presence of a source of iodine; in a first organic solvent or a mixture of organic solvents, wherein the first organic solvent is non-reactive to the source iodine; to yield the corresponding compound of formula (XI-B);

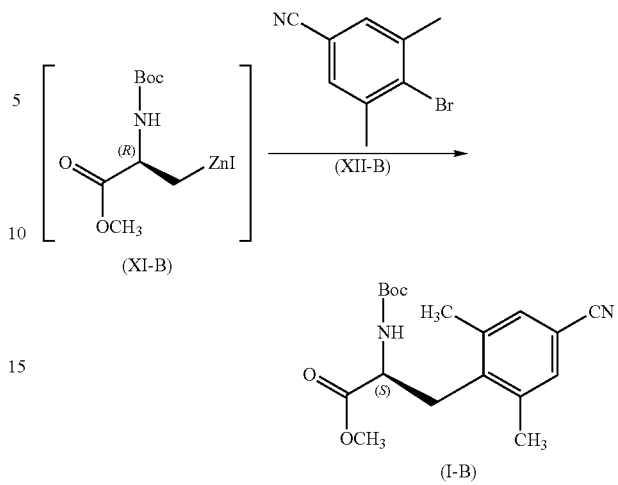

reacting the compound of formula (XI-B) with a compound of formula (XII-B); in the presence of a palladium catalyst and phosphine ligand system; in a second organic solvent or a mixture of organic solvents; to yield the corresponding compound of formula (I-B).

18. The process as in claim 17, wherein the zinc is zinc powder.

19. The process as in claim 18, wherein the zinc powder is present in an amount in the range of from about 0.5 to about 1.5 molar equivalents.

20. The process as in claim 17, wherein the source of iodine is iodine.

21. The process as in claim 20, wherein the iodine is present in an amount in the range of from about 0.1 to about 0.5 molar equivalents.

22. The process as in claim 17, wherein the first organic solvent is DMAc.

23. The process as in claim 17, wherein the compound of formula (X-B) is reacted with the zinc at a temperature of less than about 10° C.

24. The process as in claim 17, wherein the zinc and source of iodine are mixed prior to addition to the compound of formula (X-B).

25. The process as in claim 17, wherein the compound of formula (XII-B) is present in an amount in the range of from about 0.25 to about 1.0 molar equivalents.

26. The process as in claim 17, wherein the palladium catalyst and phosphine ligand system is a combination of Pd$_2$(dba)$_3$ and P(o-tol)$_3$.

27. The process as in claim 17, wherein the second organic solvent is DMAc.

28. The process as in claim 17, wherein the compound of formula (X-B) is reacted with the compound of formula (XII-B) at a temperature in the range of from about 50° C. to about 100° C.

29. The process as in claim 17, wherein the compound of formula (XI) is added to a mixture of the compound of formula (XII), the palladium catalyst and the phosphine ligand system.

30. The compound prepared according to the process of claim 17.

* * * * *